United States Patent
Streeter

(10) Patent No.: US 10,004,316 B2
(45) Date of Patent: Jun. 26, 2018

(54) PERISTALTIC HAND-HELD COSMETIC DISPENSING SYSTEM

(71) Applicant: L'Oreal, Paris (FR)

(72) Inventor: John Streeter, Redmond, WA (US)

(73) Assignee: L'Oreal, Paris (FR)

( * ) Notice: Subject to any disclaimer, the term of this patent is extended or adjusted under 35 U.S.C. 154(b) by 70 days.

(21) Appl. No.: 15/179,254

(22) Filed: Jun. 10, 2016

(65) Prior Publication Data

US 2017/0354234 A1    Dec. 14, 2017

(51) Int. Cl.
| | |
|---|---|
| *A45D 34/00* | (2006.01) |
| *A45D 34/04* | (2006.01) |
| *F04B 43/12* | (2006.01) |
| *A61M 35/00* | (2006.01) |

(52) U.S. Cl.
CPC ........... *A45D 34/041* (2013.01); *A45D 34/00* (2013.01); *A45D 34/042* (2013.01); *A61M 35/00* (2013.01); *F04B 43/12* (2013.01); *A45D 2034/005* (2013.01); *A45D 2200/10* (2013.01)

(58) Field of Classification Search
CPC .................................................. F04B 43/1253
USPC ................................ 401/40, 41, 42, 152, 155
See application file for complete search history.

(56) References Cited

U.S. PATENT DOCUMENTS

| | | | | |
|---|---|---|---|---|
| 4,717,276 A | * | 1/1988 | O'Brien | ............. B05C 17/0308 |
| | | | | 15/230.11 |
| 5,024,243 A | | 6/1991 | Snyder | |
| 5,866,108 A | | 2/1999 | LeBras et al. | |
| 6,371,674 B1 | * | 4/2002 | Lerner | .................... A46B 11/00 |
| | | | | 401/137 |
| 8,430,338 B2 | | 4/2013 | Duru et al. | |
| 8,564,778 B1 | | 10/2013 | Igarashi | |
| 8,746,586 B2 | | 6/2014 | Duru et al. | |
| 9,007,588 B1 | | 4/2015 | Igarashi | |
| 2009/0200392 A1 | | 8/2009 | Duru et al. | |
| 2015/0173488 A1 | * | 6/2015 | Witchell | .................. G01F 1/42 |
| | | | | 222/23 |
| 2016/0058156 A1 | | 3/2016 | Chiasson | |

FOREIGN PATENT DOCUMENTS

EP    2383045 A2    11/2011

OTHER PUBLICATIONS

Invitation to Pay Additional Fees With Partial Search Report dated Aug. 21, 2017, in corresponding International Application No. PCT/US2017/033854, filed May 22, 2017, 12 pages.
International Search Report and Written Opinion dated Oct. 17, 2017, in corresponding International Application No. PCT/US2017/033854, filed May 22, 2017, 17 pages.

\* cited by examiner

*Primary Examiner* — David Walczak
*Assistant Examiner* — Joshua Wiljanen
(74) *Attorney, Agent, or Firm* — Christensen O'Connor Johnson Kindness PLLC

(57) ABSTRACT

A cosmetic delivery system includes a peristaltic pump assembly having one or more wipers, the peristaltic pump assembly configured to mobilize the one or more wipers and to compress a flexible tubing received within an inner passageway partly defined by a pump casing wall, and a cosmetic applicator set having a cosmetic cartridge, the cosmetic cartridge fluidically coupled to a proximate end of the flexible tubing and an applicator connected to a distal end of the flexible tubing.

23 Claims, 5 Drawing Sheets

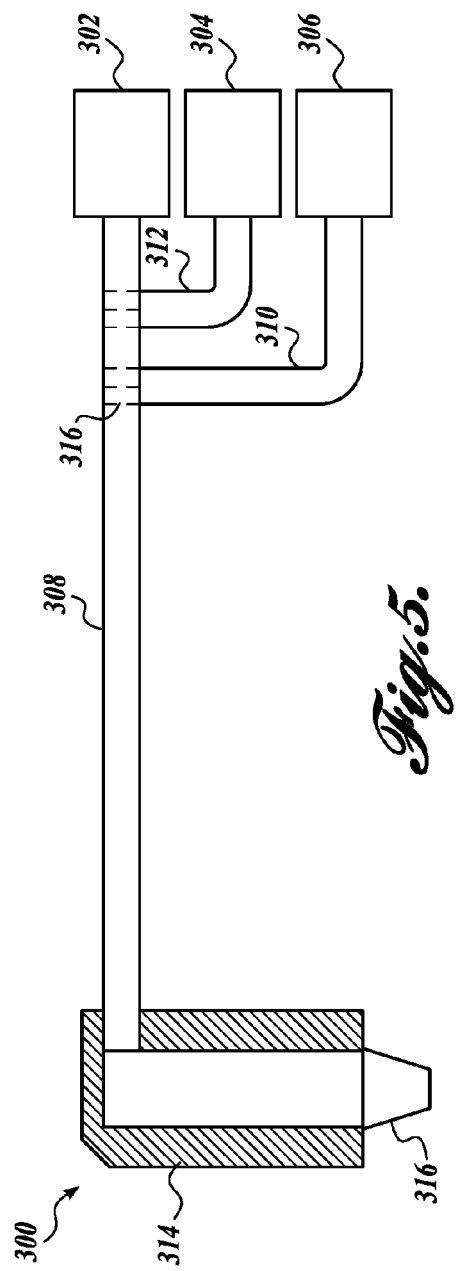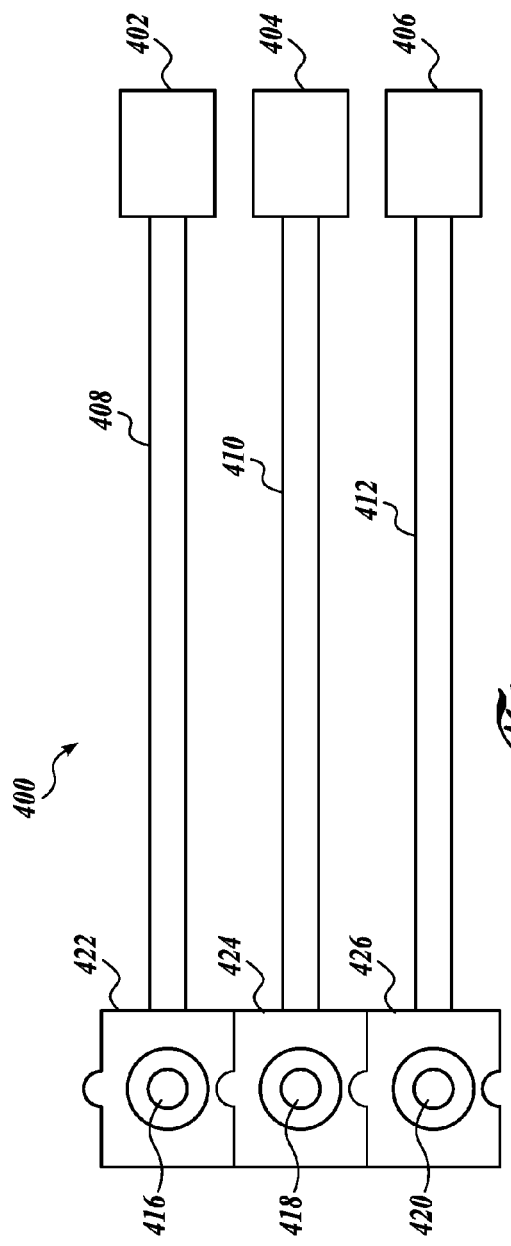

PERISTALTIC HAND-HELD COSMETIC DISPENSING SYSTEM

SUMMARY

In an aspect, the present disclosure is directed to, among other things, an electromechanical device with a peristaltic pump operable to deliver a cosmetic. In an embodiment, the electromechanical device is pre-loaded within a separately provided disposable cosmetic cartridge and tubing set. In an embodiment, a peristaltic pump drives the cosmetic without the pump coming into direct contact with any cosmetic, thus maintaining sterility, cleanliness, and delivering a cosmetic free of foreign contaminants.

In an aspect, the present disclosure is directed to, among other things, a disposable or single use cosmetic applicator set having a cosmetic cartridge, tubing, and an applicator affixed to the electromechanical device to allow direct topical application driven by the pump. In an embodiment, once exhausted of cosmetics, the cosmetic applicator set is disposed and a new and different cosmetic applicator set is loaded into the electromechanical device. In an embodiment, a variety of cosmetic applicator sets are provided with different cosmetics or different applicator tools.

In an aspect, the present disclosure is directed to, among other things, an electromechanical device for delivery of a cosmetic that does not require cleaning of the device between exhaustion of a first cosmetic and dosing a different cosmetic.

In an aspect, the present disclosure is directed to, among other things, an electromechanical device for delivery of a cosmetic configured to provide sterility, avoid contamination, and reduce clogging by maintaining a closed-loop environment.

In an aspect, the present disclosure is directed to, among other things, an electromechanical device configured to be loaded with more than one cosmetic applicator sets, wherein each set has a different cosmetic or a different applicator tool.

In an aspect, the present disclosure is directed to, among other things, an electromechanical device configured to be loaded with one of a plurality of cosmetic applicator sets, wherein each set is a different color identifying the cosmetic within.

In an aspect, the present disclosure is directed to a cosmetic delivery system, comprising a peristaltic pump assembly having one or more wipers, the peristaltic pump assembly configured to mobilize the one or more wipers and to compress a flexible tubing received within an inner passageway partly defined by a pump casing wall; and a cosmetic applicator set having a cosmetic cartridge, the cosmetic cartridge fluidically coupled to a proximate end of the flexible tubing, and an applicator connected to a distal end of the flexible tubing.

In an embodiment, the cosmetic cartridge, the flexible tubing, and the applicator are sealed to prevent contamination of the cosmetic.

In an embodiment, the applicator comprises an applicator tool selected from the group consisting of a brush, a ball roller, a sponge, and a pad.

In an embodiment, the cosmetic cartridge includes a cream, lotion, or toothpaste.

In an embodiment, the cosmetic delivery system further comprises a second cosmetic applicator set comprising a second cosmetic cartridge, the second cosmetic cartridge fluidically coupled to a proximate end of a second flexible tubing, and a second applicator connected to a distal end of the second flexible tubing.

In an embodiment, the cosmetic delivery system further comprises a second cosmetic cartridge connected to a second flexible tubing, wherein the two flexible tubings are connected to each other.

In an embodiment, the cosmetic delivery system further comprises one or more mixing baffles where the two flexible tubings are connected to each other.

In an embodiment, one of the cosmetic cartridges comprises a dried or lyophilized cosmetic and the second cosmetic cartridge comprises a liquid for reconstituting the dried or lyophilized cosmetic.

In an embodiment, the cosmetic delivery system further comprises a second cosmetic cartridge and a second flexible tubing from the second cosmetic cartridge, wherein the two flexible tubings are not connected to each other. In an embodiment, the two flexible tubings are connected to separate nozzles. In an embodiment, the separate nozzles each has a different applicator tool.

In an embodiment, the cosmetic delivery system further comprises a pressure sensor that senses the pressure within the flexible tubing.

In an embodiment, the cosmetic delivery system further comprises a valve positioned next to the flexible tubing.

In an embodiment, the cosmetic delivery system comprises a DC motor attached to the peristaltic pump. In an embodiment, the DC motor is battery powered or powered from an AC source after conversion in a AC to DC converter.

In an embodiment, the peristaltic pump assembly includes a hand crank.

In an embodiment, the cosmetic delivery system comprises a momentary switch, wherein each pressing of the momentary switch causes the motor to run for a predetermined time.

In an embodiment, the cosmetic delivery system comprises a snap-on pressure fitting that connects the applicator to the peristaltic pump assembly.

In an embodiment, the cosmetic delivery system comprises more than one separate applicator connected to the peristaltic pump assembly, and each separate applicator is connected to each other.

In an embodiment, the peristaltic pump assembly comprises one or more rollers that pinch the flexible tubing against the pump casing wall.

In an embodiment, the cosmetic delivery system provides a sterile environment.

In an embodiment, a hand-held cosmetic dispensing device comprises circuitry configured to activate a peristaltic pump assembly and to dispense a cosmetic received with a cosmetic applicator set including a cosmetic cartridge, a flexible tubing connected to the cosmetic cartridge, and an applicator connected to an end of the flexible tubing; and circuitry configured to manage at least one of a dispensing rate, a dispensing volume, and a dispensing amount of the cosmetic received with the cosmetic applicator set.

In an embodiment, a hand-held cosmetic dispensing device comprises means for peristaltically dispensing a cosmetic received with a cosmetic applicator set including a cosmetic cartridge, a flexible tubing connected to the cosmetic cartridge, and an applicator connected to an end of the flexible tubing; and means for managing at least one of a dispensing rate, a dispensing volume, and a dispensing amount of the cosmetic received with the cosmetic applicator set.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 5 is a diagrammatical illustration of a cosmetic applicator set according to one embodiment;

FIG. 6 is a diagrammatical illustration of more than one cosmetic applicator sets in an assembly according to one embodiment;

DETAILED DESCRIPTION

Automatic cosmetic dispensers frequently use mechanisms which bring mechanical parts into direct contact with the cosmetic. These dispensers are often re-used with different cosmetics requiring a thorough cleaning of the dispenser and its parts prior to re-filling with a new cosmetic. Many times the dispenser cleaning is not done properly or thoroughly, which can lead to cross-contamination, an unintended chemical reaction, the accumulation of sludge, or spoilage of the cosmetic. Typically, the entire dispensing system is discarded for a replacement including new mechanical parts. A hand-held two part system which isolates cosmetic from mechanical parts yet still automatically dispenses provides clean re-use while minimizing mechanical part waste.

In an embodiment, a "cosmetic" includes any material delivered for application. In an embodiment, the application of the cosmetic is for topical application. In an embodiment, cosmetics include lotions, creams, sunscreens, medicines, tanning lotions, skin softeners, toothpastes, and the like. In an embodiment, the cosmetic is a viscous fluid. In an embodiment, the cosmetic is a liquid. In an embodiment, the cosmetic is initially supplied as a dried or lyophilized form that is reconstituted and or mixed with liquid, such as water, an alcohol, or another cosmetic.

Figure 1:
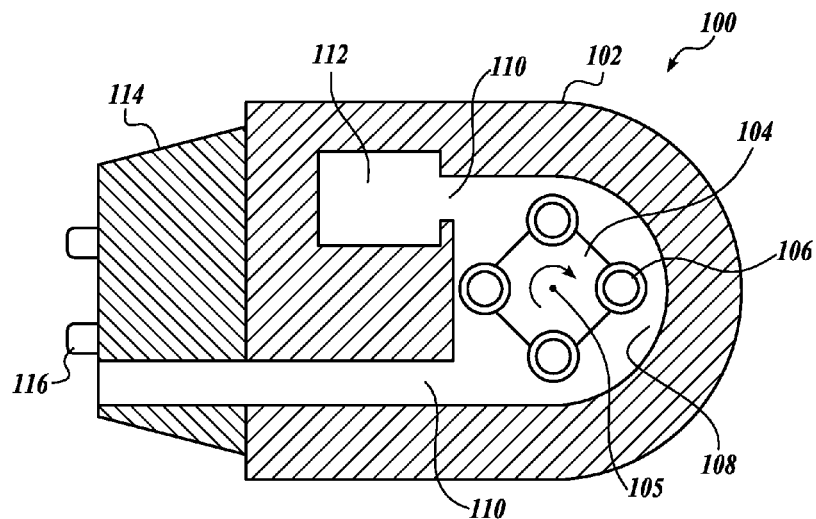
FIG. 1 is a diagrammatical illustration of an electromechanical device according to one embodiment.

Referring to FIG. 1, an electromechanical device 100 is illustrated. In an embodiment, the electromechanical device 100 is a hand-held cosmetic dispensing device. In an embodiment, the electromechanical device 100 includes a device body 102, a peristaltic pump assembly 104 and a motor 122 (shown in FIG. 9), a chamber 112 to hold a cosmetic cartridge, and a channel or passageway 110 to accommodate flexible tubing leading from the chamber 112, around the peristaltic pump assembly 104, and then to an exit point located on a connector head 114. In an embodiment, the channel or passageway 110 is the path leading from the chamber 112 out of the device, including the path around the peristaltic pump assembly 104. In an embodiment, the channel 110 is recessed. However, In an embodiment, the channel 110 is not recessed, but, the channel or passageway is defined by pegs or other detaining structure to hold the flexible tubing in place. In an embodiment, the chamber 112 is recessed. However, in an embodiment, the chamber 112 is not recessed and is defined by detaining structure for holding the cosmetic cartridge.

In an embodiment, the device body 102 is made from any material including plastic, metal, or a combination of plastics and metal. In an embodiment, the device body 102 is made from plastics, thermo plastics, polymers, resins, thermal resins, and the like, or combinations or composites thereof. Given the description herein, a person of skill will be able to fabricate the device body 102. In an embodiment, the device body 102 is constructed to hold the peristaltic pump assembly 104. In an embodiment, a peristaltic pump is a type of positive displacement pump. In an embodiment, the peristaltic pump assembly 104 in accordance with this disclosure is driven by a Direct Current (DC) or Alternating Current (AC) motor or the peristaltic pump is hand operated by having a hand crank 150. In an embodiment, the motor is battery operated, in which case the device body is formed to hold the required number of batteries. In an embodiment, a DC motor is powered by an Alternating Current source after passing through an AC to DC converter, such as a wall socket plug-in adapter. In an embodiment, the electromechanical device 102 is made to be held with one hand. In an embodiment, the electromechanical device 100 is floor or bench top mounted.

In an embodiment, the peristaltic pump assembly 104 includes one or more wipers 106 placed on a pump rotor attached to the motor through a gear reducer, for example. In the illustrated embodiment, the peristaltic pump assembly 104 is shown with four wipers 106 placed equidistant from each other on a rotor. In an embodiment, the wipers 106 include cylinder shaped rollers. In an embodiment, the wipers 106 are placed such that the wipers 106 rotate about an axis, wherein the roller axis is parallel to the rotor axis 105. In an embodiment, the peristaltic pump assembly 104 transfers fluid within a flexible tubing by repeatedly pinching the flexible tubing with the wipers 106 against the pump casing wall 108. In an embodiment, the wipers 106 are attached to swinging arms biased by springs to apply pressure against a flexible tubing placed between the wipers 106 and the pump casing wall 108 formed on one side of the casing of the peristaltic pump assembly 104. In an embodiment, the pump casing wall 108 has a depth extending in the direction of the rotor axis 105 and curvature extending around the rotor axis 105. In an embodiment, the pump casing curved wall 108 has a depth to accommodate one or more than one flexible tubings. In an embodiment, the pump casing curved wall 108 is curved for at least 180 degrees. In an embodiment, the curvature extends for greater than 180 degrees. In an embodiment, the pump casing curved wall 108 extends less than 180 degrees. In an embodiment, the pump casing curved wall 108 curves at a constant radius from the rotor axis 105. In an embodiment, the pump casing curved wall 108 defines an eccentric curve, i.e., a curve that does not have a constant radius from the rotor axis. In an embodiment, the rate of delivery of the cosmetic is varied by varying the rate of the pump rotation. In an embodiment, varying the rate of rotation of the pump is accomplished by a variable frequency drive or a rheostat.

Figure 10:
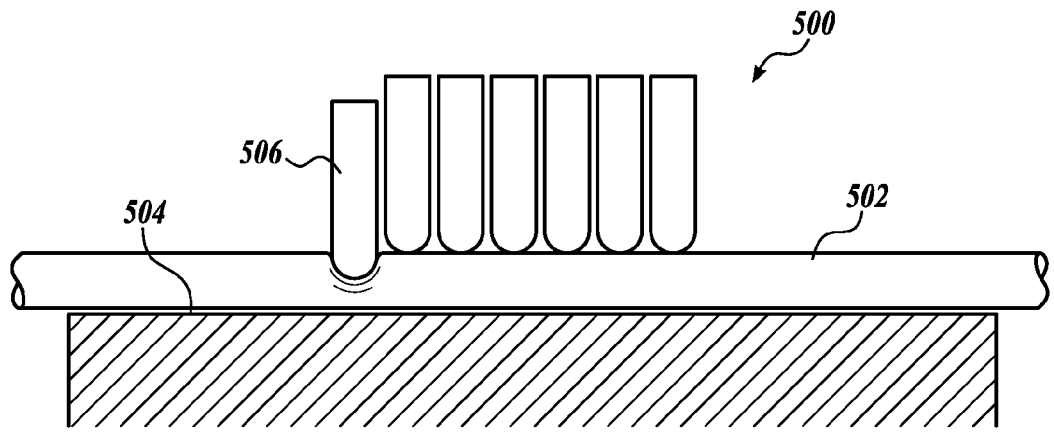
FIG. 10 is a diagrammatical illustration of a linear peristaltic pump according to one embodiment.

In an embodiment, a linear peristaltic pump is used in place of a rotating peristaltic pump. Referring to FIG. 10, in an embodiment, in a linear peristaltic pump, the pump 500 has a series of wipers 506 that are placed in series and are actuated sequentially. In an embodiment, the wipers 506 are attached to a camshaft provided with cams placed at different angles so that the wipers 506 are actuated in series. In an embodiment, the wipers 506 are actuated to resemble a rippling wave motion so as to pinch the flexible tubing 502 smoothly to transfer the fluid. The wipers 506 move linearly (up and down in FIG. 10) such that the ends of the wipers 506 pinch the flexible tubing 502 sequentially against the pump casing wall 504. In the case of the linear peristaltic pump 500, the pump casing wall 504 is flat or substantially flat. In an embodiment, the flat wall 504 includes grooves to accommodate the flexible tubing to prevent the tubing from sliding.

Referring again to FIG. 1, the device body 102 is formed so that the chamber 112 is connected to and leads into the channel 110, which includes the curved or linear pump casing wall by which the wipers pass. The channel 110 then continues from the pump casing 108 through the device body 102 to a suitable exit point on the connector head 114. In an embodiment, the channel 110 is recessed, the recess being sized to match a diameter of a flexible tubing. However, in an embodiment, the recessed channel 110 width is matched to the flexible tubing diameter and the depth of the recessed channel 110 is deep enough to accommodate two or more flexible tubings.

Figure 2:
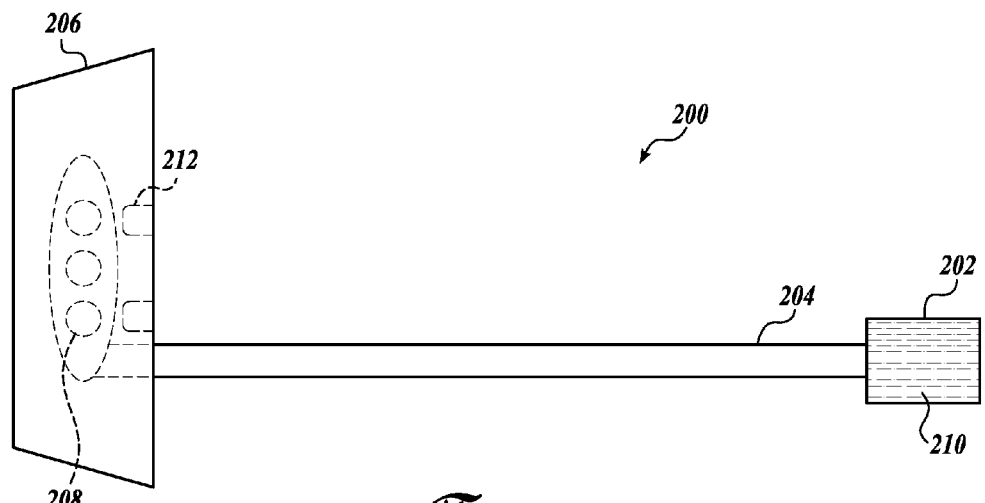
FIG. 2 is a diagrammatical illustration of a cosmetic applicator set according to one embodiment.

Referring to FIG. 2, a cosmetic applicator set 200 is illustrated. In an embodiment, a cosmetic dispensing system includes the electromechanical device 100 of FIG. 1 and the cosmetic applicator set 200 of FIG. 2. However, other embodiments of the cosmetic applicator set may be used other than the cosmetic applicator set 200. In an embodiment, the cosmetic dispensing system includes the electromechanical device and two or more cosmetic applicator sets. In this disclosure, the features of one embodiment of the electromechanical device are usable with the other embodiments, and the features of one embodiment of the cosmetic applicator set are usable with the other embodiments.

In an embodiment, the cosmetic applicator set 200 includes a cosmetic cartridge 202 containing one or a mixture of cosmetics 210 inside the cartridge 202, a flexible tubing 204 of suitable length connected at the proximate end to the cosmetic cartridge 202, and one or more applicators 206 connected to the distal end of the flexible tubing 204. In an embodiment, the cosmetic cartridge 202 is made from a variety of materials compatible with the cosmetic. In an embodiment, the cosmetic cartridge 202 is made from a plastic or metal foil or a combination of layers of plastic and foil. In an embodiment, the cosmetic cartridge is flexible or rigid. The applicator 206 includes one or more nozzles 208 through which the cosmetic 210 is dispensed. In an embodiment, the applicator 206 is made from a rigid plastic or metal to allow connecting and disconnecting the applicator 206 from the connector head 114 of the electromechanical device 100. In an embodiment, applicator tools is attached to the nozzles 208 to assist with application of the cosmetic. In an embodiment, the applicator tool is a dispensing accessory such as a brush, a roller (ball roller), sponge, or a pad, for example. In an embodiment, a suitable length of the flexible tubing 204 is a length that at least allows the flexible tubing to be loaded into the electromechanical device 100 to extend the length of the channel 110 and reach the exit of the channel at the connector head 114.

Regardless of the type of peristaltic pump used, in an embodiment, the cosmetic 210 that is to be pumped is contained within the flexible tubing 204 and does not contact any gears, lobes, impellers, or the pump casing itself. In an embodiment, the cosmetic is contained wholly within the cosmetic applicator set having the cosmetic cartridge 202, the flexible tubing 204, and the applicator 206. The flexible tubing 204 is loaded next to the curved or linear pump casing wall, such that the flexible tubing 204 is between the pump casing wall 108 and a wiper 106. The cosmetic 210 is moved through the tubing 204 and out of the applicator 206 by the compression or pinching of the tubing 204 against the pump casing wall 108 with the wipers 106.

In an embodiment, the cosmetic applicator set 200 is disposable or single-use. In an embodiment, "disposable" or "single use" means that the cosmetic cartridge is not intended to be refilled by the end user. In an embodiment, the cosmetic applicator set is sold or provided separately from the electromechanical device. In an embodiment, a variety of disposable or single use cosmetic applicator sets are supplied so that each cosmetic set is pre-loaded with a different type of cosmetic. Additionally, in an embodiment, cosmetic applicator sets containing the same cosmetic or mixture are provided with different applicator tools. To change from dispensing different cosmetics from the same electromechanical device, the entire cosmetic applicator set is replaced with a different cosmetic applicator set. In an embodiment, the cosmetic applicator sets have a color to represent the same cosmetic. In an embodiment, cosmetic applicator sets having the same cosmetic have the same color but have different applicator tools.

Figure 3:
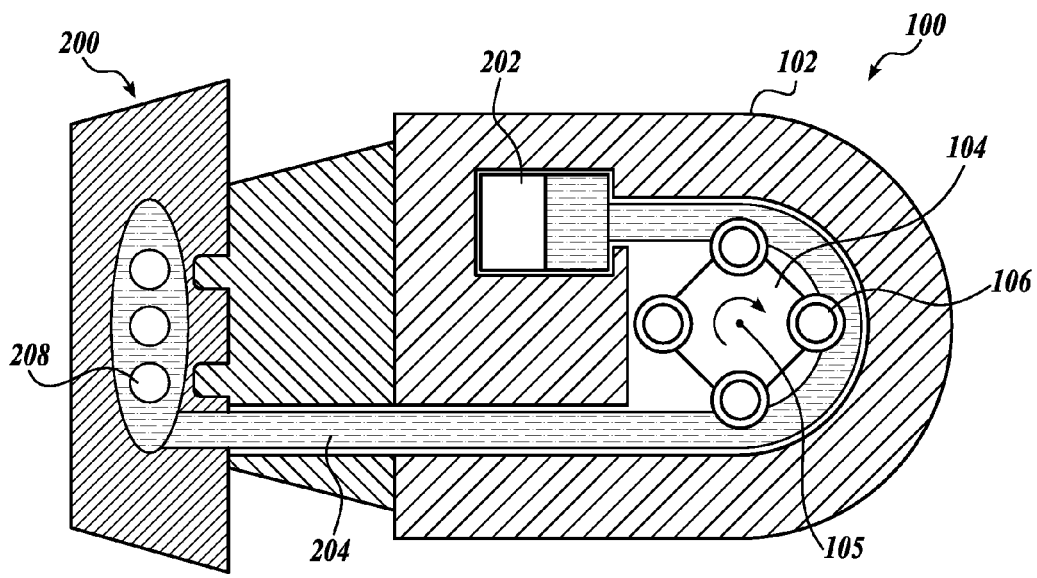
FIG. 3 is a diagrammatical illustration of a cosmetic dispensing system comprising the electromechanical device and the cosmetic applicator set according to one embodiment.
Figure 4:
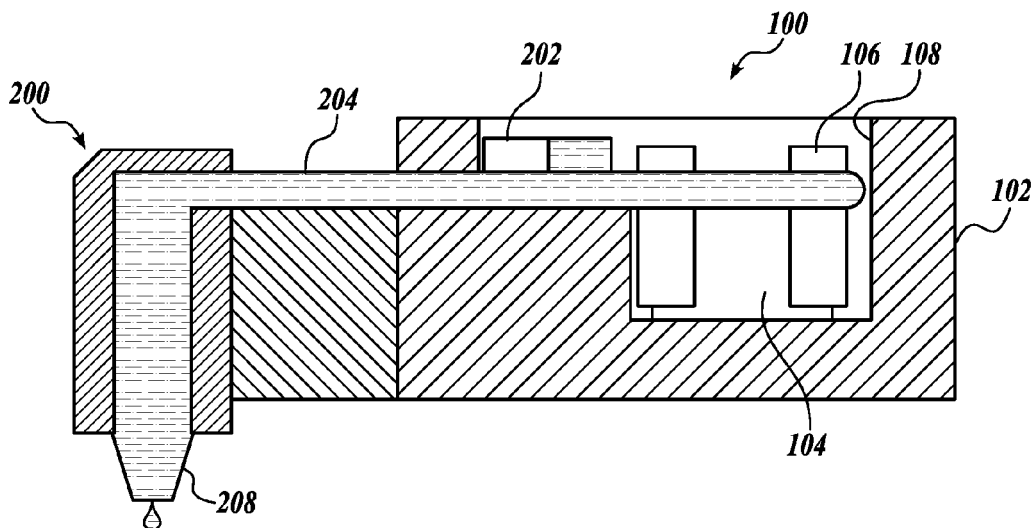
FIG. 4 is a diagrammatical illustration of a cosmetic dispensing system comprising the electromechanical device and the cosmetic applicator set according to one embodiment.

Referring to FIGS. 3 and 4, in an embodiment, the disposable or single use cosmetic applicator set 200 is loaded into the electromechanical device 100 for dispensing the cosmetic 210. The cosmetic cartridge 202 is loaded into the chamber 112. The flexible tubing 204 is loaded into the channel 110 including the area next to the curved wall 108 of the pump casing to lie between the pump casing wall 108 and the wipers 106 to allow pinching by the wipers 106. The applicator 206 is attached to the device body 102 at the connector head 114. In an embodiment, the connector head 114 includes one or more snap-on pressure fittings 116. In an embodiment, the applicator 206 includes recessed holes 212 that mate with the pressure fittings 116. In an embodiment, after loading a cosmetic applicator set 200 into the electromechanical device 100, the user then starts the peristaltic pump assembly 104 to dispense the cosmetic 210 through the applicator nozzles 208. In an embodiment, the applicator nozzle 208 have a thin, easily broken membrane that maintains the cosmetic 210 in a sterile state until dispensed. In an embodiment, the membrane is broken by the pressure generated by the peristaltic pump assembly 104. Alternatively, in an embodiment, the membrane is broken by the act of attaching an applicator tool to the end of the nozzle, or the membrane is be pierced by the user. In an embodiment, applicator tools are snap-on or screw-on type accessories.

In an embodiment, the device body 102 does not have a reservoir that is to be filled and re-filled with various cosmetics. Instead, In an embodiment, the cosmetic is contained within the cosmetic cartridge, and the cosmetic cartridge is loaded into the pump. This allows the cosmetics that are dispensed to remain sterile and free of contamination.

In an embodiment, the applicator 206 includes one or more nozzles 208. In an embodiment, the applicator 206 has valves to select which one of a plurality of nozzles is to receive the cosmetic. In an embodiment, the applicator 206 includes a plurality of nozzles, wherein each nozzle has a different applicator tool. In an embodiment, the applicator 206 includes a single nozzle 208 to which interchangeable applicator tools are be affixed.

Referring to FIG. 5, in an embodiment, the cosmetic applicator set 300 has more than one cosmetic cartridge 302, 304, and 306. In an embodiment, each cosmetic cartridge 302, 304, and 306 has a different cosmetic inside. Each cosmetic cartridge 302, 304, and 306 is connected to a single flexible tubing 308, which in turn leads to the applicator 314 and nozzle 316. For example, cosmetic cartridge 304 connects to flexible tubing 308 via the flexible tubing 312. Cosmetic cartridge 306 connects to flexible tubing 308 via flexible tubing 310. In an embodiment, where one flexible tubing of a first cosmetic cartridge connects to another flexible tubing of a different cosmetic cartridge, a baffle or mixer is placed at the juncture on the inside of the flexible tubing. For example, baffles 316 are placed where flexible tubings 310 and 312 connect to flexible tubing 308. In an embodiment, the mixer or baffles are vanes, ribs, or fins, arranged in whorls or in a cork-screw manner. In an embodiment, the connection of the flexible tubings 310 and 312 to 308 take place before the peristaltic pump assembly 104.

In an embodiment, a cosmetic cartridge contains a cosmetic that is dried or lyophilized. In an embodiment, for the case of dried or lyophilized cosmetics, one or more cosmetic cartridges contain a liquid, such as water or alcohol, that is automatically mixed with the dried or lyophilized cosmetic to reconstitute the dried or lyophilized cosmetic upon operating the pump. In an embodiment, dried or lyophilized cosmetics are reconstituted by the user by introducing and mixing the cosmetic with the reconstituting liquid manually.

In an embodiment, the electromechanical device 100 accommodates more than one cosmetic applicator set. Referring to FIG. 6, a plurality of cosmetic applicator sets are grouped into an assembly 400. Each cosmetic applicator set includes a separate a cosmetic cartridge 402, 404, and 406. Each cosmetic applicator set includes a separate flexible tubing 408, 410, and 412, respectively. Each cosmetic applicator set includes a separate applicator 422, 424, and 426 and nozzle 416, 418, and 420, respectively. The applicator is a composite of applicators 422, 424, and 426 that snap together to each other and to the connector head 114 on the electromechanical device 100. In an embodiment, each nozzle 416, 418, and 420 includes the same or a different applicator tool, such as a brush, roller, or pad. In an embodiment, the electromechanical device 100 includes separate valves to allow the user to control which of the cosmetics is to be dispensed. Alternatively, in an embodiment, two or more cosmetics are dispensed simultaneously. This may be desirable where cosmetics can react with each other and therefore, it is advantageous to avoid mixing prior to dispensing. In an embodiment, the two or more cosmetic cartridges 402, 404, and 406 have the same cosmetic, but, the applicator tool for each nozzle 416, 418, and 420 is different.

Figure 7:
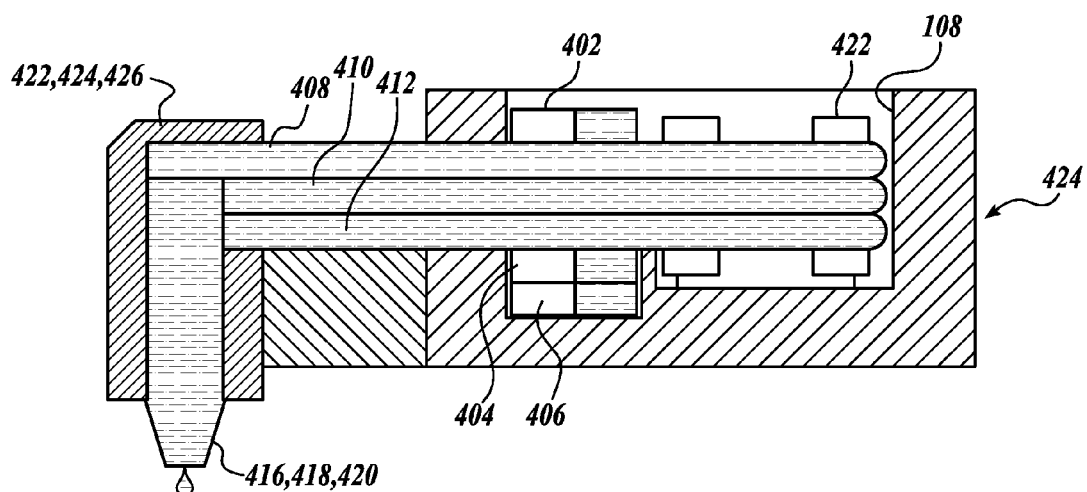
FIG. 7 is a diagrammatical illustration of a cosmetic dispensing system comprising the electromechanical device and more than one cosmetic applicator sets according to one embodiment.

Referring to FIG. 7, an electromechanical device 424 is illustrated in which more than one cosmetic applicator sets are loaded, such as the cosmetic applicator sets of FIG. 6. The electromechanical device 424 includes cosmetic cartridges 402, 404, and 406 loaded into the same or a separate chamber. The electromechanical device 424 includes more than one flexible tubings 408, 410, and 412. In an embodiment, the wiper 432 is of sufficient length so that the wiper 432 pinches the more than one flexible tubings 408, 410, and 412 at the same time against the pump casing wall 108. The electromechanical device 424 includes the more than one applicators 422, 424, and 426, each of which has a nozzle 416, 418, and 420, respectively. In an embodiment, when one or more flexible tubings are loaded in the electromechanical device 424, the channel or passageway, including the pump casing wall, has indentations or grooves to assist with maintaining the flexible tubings in place and prevent the tubings from sliding. In an embodiment, when two or more cosmetic applicator sets are loaded into the same electromechanical device, the cosmetic cartridges are loaded into the same cosmetic chamber or each cosmetic cartridge is loaded into a separate chamber within the device body. In an embodiment, when two or more cosmetic applicator sets are loaded into the same electromechanical device, the flexible tubing of each cosmetic applicator set is loaded into the same or different channel.

Figure 8:
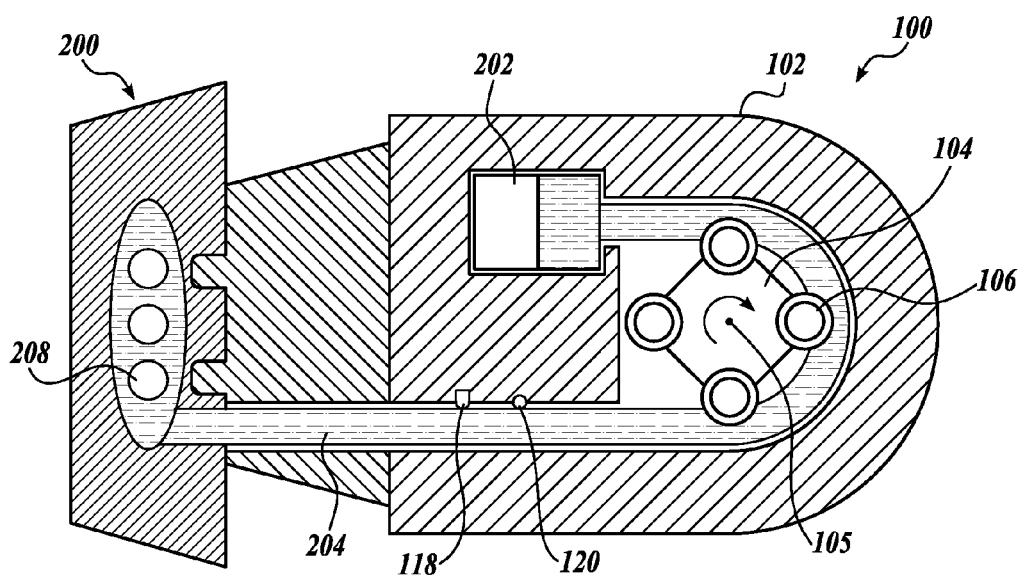
FIG. 8 is a diagrammatical illustration of a cosmetic dispensing system comprising the electromechanical device and a cosmetic applicator set according to one embodiment.

Referring to FIG. 8, in an embodiment, the electromechanical device 100 includes a sensor 120. In an embodiment, a sensor 120 is a pressure sensor that detects the pressure of the flexible tubing 204. In an embodiment, a pressure sensor 120 detects a blockage at the applicator 200 or nozzle 208. Further, in an embodiment, a pressure sensor 120 detects low pressure indicating a blockage upstream of the peristaltic pump assembly 104 or a leak or a pump not operating properly. In an embodiment, the electromechanical device includes one or more than one valves to shut off flow to one or more nozzles. In an embodiment, the valve 118 is activated by a solenoid. When activated, in an embodiment the valve 118 pinches the flexible tubing 204 to shut off the flow for the particular flexible tubing 204.

Figure 9:
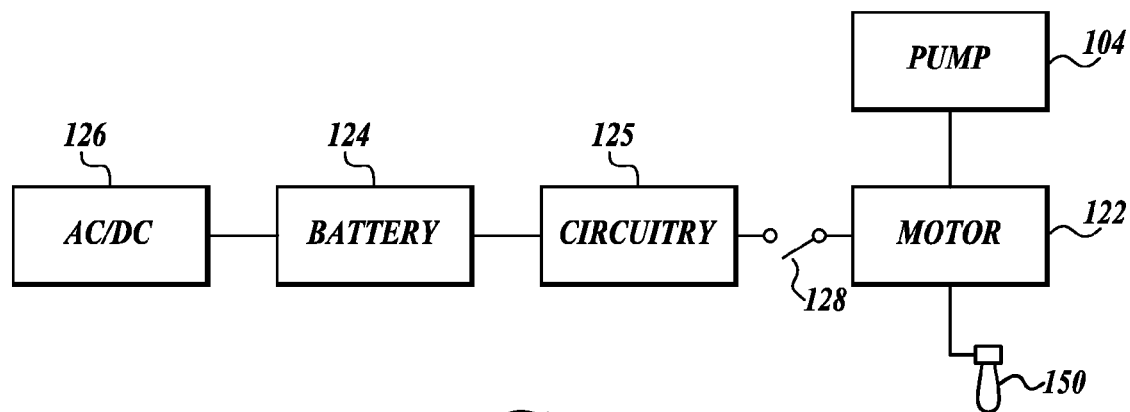
FIG. 9 is a schematic illustration of a pump system for the electromechanical device according to one embodiment.

Referring to FIG. 9, a schematic illustration of an electrical system of the electromechanical device 100 is shown. The peristaltic pump assembly 104 is connected to a motor 122. In an embodiment, the motor 122 is a DC motor or an AC motor. In an embodiment, the motor 122 is omitted or is optional, and a hand crank 150 is used to turn the peristaltic pump assembly 104. In an embodiment, the motor 122 is powered by a battery 124. In an embodiment, the motor 122 is powered by an AC source, such as a wall socket, after rectification by an AC to DC plug-in wall adapter 126. In an embodiment, the battery 124 is also be recharged by plugging the wall adaptor 126 connected to the battery. In an embodiment, the electromechanical device includes an switch 128 to provide power to the motor 122. In an embodiment, the switch 128 is an on-off switch. In an embodiment, the switch 128 is a momentary switch. In an embodiment, the switch 128 is operated by circuitry 125. In the embodiments where the electromechanical device includes one or more sensors or one or more valves, the sensors and valves are powered by the batteries 124. In an embodiment, the hand-held dispensing device include circuitry 125 to manage at least one of a dispensing rate, a dispensing volume, and a dispensing amount of the cosmetic received with the cosmetic applicator set. In an embodiment, for example, the circuitry 125 adjusts voltage using an electronic speed control (ESC) thereby reducing the speed and flow rate of the pump 104. In an embodiment, for example, the circuitry 125 integrates the dispensed flow using an integrator, and shuts-off the pump when the integrated amount of flow reaches a pre-selected value.

In an embodiment, the electromechanical device 100 includes a power source. In an embodiment, the power source is operably coupled to one or more components, modules, circuitry, sensors, and the like of the electromechanical device 100. Non-limiting examples of power sources examples include one or more button cells, chemical battery cells, a fuel cell, secondary cells, lithium ion cells, micro-electric patches, nickel metal hydride cells, silver-zinc cells, capacitors, super-capacitors, thin film secondary cells, ultra-capacitors, zinc-air cells, and the like. In an embodiment, the electromechanical device 100 is inductively coupled to a power source via one or more antennas. In an embodiment, the power source is electromagnetically, magnetically, acoustically, optically, inductively, electrically, or capacitively coupled to one or more components, modules, circuitry, sensors, and the like of the electromechanical device 100.

In an embodiment, a hand-held cosmetic dispensing device 100 comprises circuitry 125 configured to activate a peristaltic pump assembly 104 and to dispense a cosmetic 210 received with a cosmetic applicator set 200 including a cosmetic cartridge 202, a flexible tubing 204 connected to the cosmetic cartridge, and an applicator 206 connected to an end of the flexible tubing; and circuitry 125 configured to manage at least one of a dispensing rate, a dispensing volume, and a dispensing amount of the cosmetic received with the cosmetic applicator set.

In an embodiment, a hand-held cosmetic dispensing device 100 comprises means 104 for peristaltically dispensing a cosmetic 210 received with a cosmetic applicator set 200 including a cosmetic cartridge 202, a flexible tubing 204 connected to the cosmetic cartridge, and an applicator 206 connected to an end of the flexible tubing; and means 125 for managing at least one of a dispensing rate, a dispensing volume, and a dispensing amount of the cosmetic received with the cosmetic applicator set.

In an embodiment, the electromechanical device 100 delivers a single or multiple doses. For example, in an embodiment, a momentary switch is used to deliver a measured dose, wherein each pressing of the momentary switch multiplies the dose proportionately. For example, in an embodiment, each pressing of the momentary switch adds a predetermined time to a timer. The motor then runs for the pre-determined time multiplied by the number of pressings of the momentary switch. Peristaltic pumps are considered positive displacement pumps and can deliver measured amounts of cosmetic per unit time. In an embodiment, the peristaltic pump assembly 104 is run in reverse to remove material, for example, if excess is applied.

The electromechanical device and the cosmetic applicator sets make possible a method of dispensing a cosmetic with a sterile environment. In an embodiment, the method of dispensing a cosmetic with a sterile environment includes dispensing a cosmetic from a cosmetic applicator set, wherein the cosmetic applicator set comprises a cosmetic cartridge containing the cosmetic with a sterile environment, a flexible tubing connected to the cosmetic cartridge, and an applicator connected to an end of the flexible tubing.

In an embodiment, the method of dispensing a cosmetic with a sterile environment further includes dispensing the cosmetic with a sterile environment from the cosmetic applicator set, wherein the cosmetic applicator set is loaded into an electromechanical device, wherein the electromechanical device comprises a device body, a peristaltic pump within the device body, wherein the peristaltic pump includes a pump casing wall by which one or more wipers pass as the pump rotates, a chamber within the device body, and a channel within the device body, wherein the channel leads from the chamber past the pump casing wall and from the pump casing wall to an exit point, and wherein the cosmetic cartridge is in the chamber, and the flexible tubing is in the channel passes between the pump casing wall and at least one wiper.

In an embodiment, the method of dispensing a cosmetic with a sterile environment further includes replacing the cosmetic applicator set that has been exhausted with a second cosmetic applicator set to dispense a second cosmetic, wherein the second cosmetic applicator set comprises a second cosmetic cartridge, a second flexible tubing, and a second applicator.

In an aspect, the present disclosure is directed to a cosmetic delivery system 100, comprising a peristaltic pump assembly 104 having one or more wipers 106, the peristaltic pump assembly 104 is configured to mobilize the one or more wipers 106 and to compress a flexible tubing 204 received within an inner passageway 110 partly defined by a pump casing wall 108; and a cosmetic applicator set 200 having a cosmetic cartridge 202, the cosmetic cartridge 202 fluidically coupled to a proximate end of the flexible tubing 204, and an applicator 206 connected to a distal end of the flexible tubing 204.

In an embodiment, the cosmetic cartridge 202, the flexible tubing 204, and the applicator 206 are sealed to prevent contamination of the cosmetic.

In an embodiment, the applicator 206 comprises an applicator tool 208 selected from the group consisting of a brush, a ball roller, a sponge, and a pad.

In an embodiment, the cosmetic cartridge 202 includes a cream 210, lotion, or toothpaste.

In an embodiment, the cosmetic delivery system 100 further comprises a second cosmetic applicator set comprising a second cosmetic cartridge (404, 406), the second cosmetic cartridge fluidically coupled to a proximate end of a second flexible tubing (410, 412), and a second applicator (424, 426) connected to a distal end of the second flexible tubing.

In an embodiment, the cosmetic delivery system 100 further comprises a second cosmetic cartridge (304, 306) connected to a second flexible tubing (312, 310), wherein the two flexible tubings are connected to each other.

In an embodiment, the cosmetic delivery system 100 further comprises one or more mixing baffles (312, 310) where the two flexible tubings are connected to each other.

In an embodiment, one of the cosmetic cartridges comprises a dried or lyophilized cosmetic and the second cosmetic cartridge comprises a liquid for reconstituting the dried or lyophilized cosmetic.

In an embodiment, the cosmetic delivery system 100 further comprises a second cosmetic cartridge (404, 406) and a second flexible tubing (410, 412) from the second cosmetic cartridge, wherein the two flexible tubings are not connected to each other.

In an embodiment, the two flexible tubings (410, 412) are connected to separate nozzles (418, 420).

In an embodiment, the separate nozzles (418, 420) each has a different applicator tool (418, 420).

In an embodiment, the cosmetic delivery system 100 further comprises a pressure sensor 120 that senses the pressure within the flexible tubing.

In an embodiment, the cosmetic delivery system 100 further comprises a valve 118 positioned next to the flexible tubing 204.

In an embodiment, the cosmetic delivery system 100 comprises a DC motor 122 attached to the peristaltic pump assembly 204.

In an embodiment, the DC motor 122 is battery powered or powered from an AC source after conversion in a AC to DC converter 126.

In an embodiment, the peristaltic pump assembly 204 includes a hand crank 150.

In an embodiment, the cosmetic delivery system 100 comprises a momentary switch 128, wherein each pressing of the momentary switch causes the motor to run for a predetermined time.

In an embodiment, the cosmetic delivery system 100 comprises a snap-on pressure fitting 116 that connects the applicator 206 to the peristaltic pump assembly 204.

In an embodiment, the cosmetic delivery system 100 comprises more than one separate applicator (422, 424, 426) connected to the peristaltic pump assembly 104, and each separate applicator is connected to each other.

In an embodiment, the peristaltic pump assembly 104 comprises one or more rollers 106 that pinch the flexible tubing 204 against the pump casing wall 108.

In an embodiment, the cosmetic delivery system 100 provides a sterile environment.

In an embodiment, a hand-held cosmetic dispensing device 100 comprises circuitry 125 configured to activate a peristaltic pump assembly 104 and to dispense a cosmetic 210 received with a cosmetic applicator set 200 including a cosmetic cartridge 202, a flexible tubing 204 connected to the cosmetic cartridge, and an applicator 206 connected to an end of the flexible tubing; and circuitry 125 configured to manage at least one of a dispensing rate, a dispensing volume, and a dispensing amount of the cosmetic received with the cosmetic applicator set.

In an embodiment, a hand-held cosmetic dispensing device 100 comprises means 104 for peristaltically dispensing a cosmetic 210 received with a cosmetic applicator set 200 including a cosmetic cartridge 202, a flexible tubing 204 connected to the cosmetic cartridge, and an applicator 206 connected to an end of the flexible tubing; and means 125 for managing at least one of a dispensing rate, a dispensing volume, and a dispensing amount of the cosmetic received with the cosmetic applicator set.

While illustrative embodiments have been illustrated and described, it will be appreciated that various changes can be made therein without departing from the spirit and scope of the invention.

The embodiments of the invention in which an exclusive property or privilege is claimed are defined as follows:

1. A cosmetic delivery system, comprising:
    a peristaltic pump assembly having one or more wipers, the peristaltic pump assembly configured to mobilize the one or more wipers and to compress a flexible tubing received within an inner passageway partly defined by a pump casing wall; and
    a replaceable cosmetic applicator set having a cosmetic cartridge, a flexible tubing wherein the cosmetic cartridge is fluidically coupled to a proximate end of the flexible tubing, and an applicator connected to a distal end of the flexible tubing, wherein the cosmetic cartridge, the tubing, and the applicator are provided as a set sealed to each other.

2. The cosmetic delivery system of claim 1, wherein the cosmetic cartridge, the flexible tubing, and the applicator are sealed to prevent contamination of the cosmetic.

3. The cosmetic delivery system of claim 1, wherein the applicator comprises an applicator tool selected from the group consisting of a brush, a ball roller, a sponge, and a pad.

4. The cosmetic delivery system of claim 1, wherein the cosmetic cartridge includes a cream, lotion, or toothpaste.

5. The cosmetic delivery system of claim 1, further comprising a second cosmetic applicator set including:
    a second cosmetic cartridge, the second cosmetic cartridge fluidically coupled to a proximate end of a second flexible tubing, and a second applicator connected to a distal end of the second flexible tubing.

6. The cosmetic delivery system of claim 1, further comprising a second cosmetic cartridge connected to a second flexible tubing, wherein the two flexible tubings are connected to each other.

7. The cosmetic delivery system of claim 6, comprising one or more mixing baffles where the two flexible tubings are connected to each other.

8. The cosmetic delivery system of claim 1, further comprising a second cosmetic cartridge and a second flexible tubing from the second cosmetic cartridge, wherein the two flexible tubings are not connected to each other.

9. The cosmetic delivery system of claim 8, wherein the two flexible tubings are connected to separate nozzles.

10. The cosmetic delivery system of claim 1, further comprising a pressure sensor that senses the pressure within the flexible tubing.

11. The cosmetic delivery system of claim 1, further comprising a valve positioned next to the flexible tubing.

12. The cosmetic delivery system of claim 1, comprising a DC motor attached to the peristaltic pump assembly.

13. The cosmetic delivery system of claim 12, wherein the DC motor is battery powered or powered from an AC source after conversion in a AC to DC converter.

14. The cosmetic delivery system of claim 1, wherein the peristaltic pump assembly includes a hand crank.

15. The cosmetic delivery system of claim 1, comprising a momentary switch, wherein each pressing of the momentary switch causes the motor to run for a predetermined time.

16. The cosmetic delivery system of claim 1, comprising a snap-on pressure fitting that connects the applicator to the peristaltic pump assembly.

17. The cosmetic delivery system of claim 1, comprising more than one separate applicator connected to the peristaltic pump assembly, and each separate applicator is connected to each other.

18. The cosmetic delivery system of claim 1, wherein the peristaltic pump assembly comprises one or more rollers that pinch the flexible tubing against the pump casing wall.

19. The cosmetic delivery system of claim 1, wherein the cosmetic delivery system provides a sterile environment.

20. A cosmetic delivery system, comprising:
    a peristaltic pump assembly having one or more wipers, the peristaltic pump assembly configured to mobilize the one or more wipers and to compress a flexible tubing received within an inner passageway partly defined by a pump casing wall;
    a cosmetic applicator set having a cosmetic cartridge, the cosmetic cartridge fluidically coupled to a proximate end of the flexible tubing;
    an applicator connected to a distal end of the flexible tubing;

a second cosmetic cartridge connected to a second flexible tubing, wherein the two flexible tubings are connected to each other, and wherein one of the cosmetic cartridges comprises a dried or lyophilized cosmetic and the second cosmetic cartridge comprises a liquid for reconstituting the dried or lyophilized cosmetic.

21. A cosmetic delivery system, comprising:
a peristaltic pump assembly having one or more wipers, the peristaltic pump assembly configured to mobilize the one or more wipers and to compress a flexible tubing received within an inner passageway partly defined by a pump casing wall;
a cosmetic applicator set having a cosmetic cartridge, the cosmetic cartridge fluidically coupled to a proximate end of the flexible tubing;
an applicator connected to a distal end of the flexible tubing;
a second cosmetic cartridge and a second flexible tubing from the second cosmetic cartridge, wherein the two flexible tubings are not connected to each other;
wherein the two flexible tubings are connected to separate nozzles; and
wherein the separate nozzles each has a different applicator tool.

22. A hand-held cosmetic dispensing device, comprising:
circuitry configured to activate a peristaltic pump assembly and to dispense a cosmetic received with a replaceable cosmetic applicator set including a cosmetic cartridge, a flexible tubing connected to the cosmetic cartridge, and an applicator connected to an end of the flexible tubing, wherein the cosmetic cartridge, the tubing, and the applicator are provided as a set sealed to each other; and
circuitry configured to manage at least one of a dispensing rate, a dispensing volume, and a dispensing amount of the cosmetic received with the cosmetic applicator set.

23. A hand-held cosmetic dispensing device, comprising:
means for peristaltically dispensing a cosmetic received with a replaceable cosmetic applicator set including a cosmetic cartridge, a flexible tubing connected to the cosmetic cartridge, and an applicator connected to an end of the flexible tubing, wherein the cosmetic cartridge, the tubing, and the applicator are provided as a set sealed to each other; and
means for managing at least one of a dispensing rate, a dispensing volume, and a dispensing amount of the cosmetic received with the cosmetic applicator set.

* * * * *